United States Patent
Wunsch et al.

(10) Patent No.: US 6,370,973 B1
(45) Date of Patent: Apr. 16, 2002

(54) DEVICE FOR REMOVING SLAG SAMPLES

(75) Inventors: Hartmut Wunsch; Gerhard Wunsch, both of Mettmann (DE)

(73) Assignee: Midwest Instrument Co., Inc., Hartland, WI (US)

( * ) Notice: Subject to any disclaimer, the term of this patent is extended or adjusted under 35 U.S.C. 154(b) by 0 days.

(21) Appl. No.: 09/580,009

(22) Filed: May 26, 2000

Related U.S. Application Data

(63) Continuation-in-part of application No. PCT/EP98/07683, filed on Nov. 27, 1998.

(30) Foreign Application Priority Data

Jun. 1, 1999 (DE) .......................................... 299 09 595

(51) Int. Cl.⁷ ................................................. G01N 1/12
(52) U.S. Cl. .................................. 73/864.53; 73/864.55
(58) Field of Search ........................ 73/864.53, 864.55, 73/864.58, 863.11, 864.54, 864.56, 865.59; 374/139

(56) References Cited

U.S. PATENT DOCUMENTS

| | | | |
|---|---|---|---|
| 3,295,171 A | * 1/1967 | Strange et al. ........... | 73/863.52 |
| 3,877,309 A | 4/1975 | Hance | |
| 3,985,031 A | * 10/1976 | Franz ....................... | 73/863.11 |
| 4,002,073 A | * 1/1977 | Collins .................... | 73/864.57 |
| 4,055,086 A | * 10/1977 | Collins .................... | 73/864.57 |
| 4,102,197 A | 7/1978 | Bardenheuer et al. | |
| 4,428,245 A | * 1/1984 | Nakamura et al. ....... | 73/864.52 |
| 4,557,152 A | 12/1985 | Plessers et al. | |
| 5,577,841 A | * 11/1996 | Wall ........................... | 374/140 |

FOREIGN PATENT DOCUMENTS

| | | | | |
|---|---|---|---|---|
| GB | 1466071 | * | 3/1977 | ............... 73/864.55 |
| JP | 61271452 | | 1/1985 | |
| SU | 646215 | | 5/1979 | |

* cited by examiner

Primary Examiner—Hezron Williams
Assistant Examiner—C D Garber
(74) Attorney, Agent, or Firm—Ryan Kromholz & Manion, S.C.

(57) ABSTRACT

The invention relates to a probe for removing slag samples from iron- or steel-making plants which has an inlet opening underneath the sample chamber, at least one region of the inlet opening having a small cross section in relation to the sample chamber, while the preferably cylindrical sample chamber has a small height in relation to its cross section.

11 Claims, 5 Drawing Sheets

DEVICE FOR REMOVING SLAG SAMPLES

This application is a continuation-in-part of copending International Patent Application PCT/EP98/07683 filed Nov. 27, 1998. A right of priority is also claimed as to co-pending German Utility Application No. 299 09 595.9 filed on Jun. 1, 1999.

BACKGROUND OF THE INVENTION

The invention relates to a device for removing liquid media, in particular slag samples, from molten metal baths in iron or steel-making plants.

For removing samples of pig iron slag, for example, from a channel, flue or ladle, or for removing samples of steel slag from a converter, ladle, electrolytic refining furnace or treatment plant, there are various known methods for obtaining samples which are used for spectrometric analysis, but which have to be processed into a coin-shaped slag sample by means of a complex process.

Thus, according to one known method of slag sample removal, first of all a steel rod or similar metal implement is dipped into the molten metal. Simple steel tubes, steel rods or else more complicatedly shaped elements of greater surface area, which may be fastened on the outside of a dip sampling or dip temperature probe, may be used for this. When the metal implement is drawn out of the molten metal, the slag remains adhering to the metal surface. To prepare the slag sample for analysis, the slag must be knocked off the metal implement and the individual pieces of slag have to be processed further to form coin-shaped samples.

The processing of the slag may in some cases take up to one hour and makes this method of sample removal time- and cost-intensive. In addition to the high processing effort, false readings in the results of the analysis may also occur as a result of impure samples if the removal probes are used repeatedly and are consequently contaminated. In general, although the residual slag of the previous sample removal is thoroughly removed from the surface of the removal probe, in practice, false measured value readings caused by slag residues can scarcely be avoided.

Further false measured values are attributable to additives such as binders which have to be introduced into the slag sample during its preparation for analysis.

Such sample removal processes are described in U.S. Pat. No. 5,435,196.

This widely used procedure, consequently, still does not produce satisfactory results. In a novel method, the slag sample is sucked off of the surface of the molten metal with the aid of a suction probe. The probe essentially corresponds in its structural design to the probes used for sample removal from steel molten metal.

However, unlike the case of steel sample removal, the probe cannot be dipped into the molten metal, but instead has to be positioned with its inlet opening precisely in the layer of slag. This presents considerable difficulties in the case of thin layers of slag, since contamination of the sample with liquid metal can be avoided only with great difficulty. Sample removal with the aid of a suction probe is also scarcely possible in the case of certain metallurgical vessels, such as converters or treatment plants for example, on account of positioning difficulties. If the probe is dipped in too deeply, so that molten metal also gets into the sample mold, the slag sample is unusable for analysis.

The slag samples obtained are brittle and tend to crack, which may lead to fracturing of the samples. The samples can then no longer be used for spectrometric analysis.

Sample probes known in the art of steel sample removal, for example, with a cooling plate for the sample, also cannot be used for the removal of slag samples. Although such probes provide a sample of the molten steel that can be successfully analyzed, in that the steel forms a usable analysis surface on the cooling plate, such a probe usually does not produce slag samples which can be used for slag analysis, since the cooled slag on the cooling plate fractures or cracks and then can no longer be used for analysis.

Problems related to the dipping depth also do not exist in the case of steel sample removal, since the steel sample probe can be dipped into the molten metal to any desired depth to remove a steel sample, without risk, as in the case of slag sample removal, of contamination of the sample on account of incorrect positioning of the removal probe. Even with careful positioning of a steel sample probe in the slag layer, a pure slag sample can seldom be obtained.

SUMMARY OF THE INVENTION

The invention is therefore based on solving the problem of providing a removal device which allows simple and reliable slag sample removal from molten metals.

The problem is solved by providing a device for removing liquid media, in particular slag samples, which has an inlet opening located below the sample chamber, the cross section of the inlet opening being small, at least in one region, in relation to the cross section of the sample chamber, while the preferably cylindrically shaped sample chamber has a small height in relation to its cross section.

When the sample removal device is dipped into the layer of slag, the sample chamber is filled with slag through the inlet opening (mold inlet) located below the sample chamber. As this happens, an analysis surface forms against the cooling plate which forms the upper interior surface of the sample chamber. Contamination by the molten metal is prevented because the slag always enters the sample chamber first, on account of its lower specific gravity or density in comparison with that of the molten metal. The sample chamber is preferably shaped with respect to its volume in such a way that it is in any event completely filled only with slag, irrespective of the dipping depth of the sample probe.

The mold inlet, shaped narrower in comparison with the sample chamber, results in there being a highly distinct separating plane between slag and steel, even if a slag sample is taken from a layer of slag that is very thin and steel thus also gets into the inlet. The diameter of the inlet is dimensioned such that the slag located in the sample chamber freezes and cannot run back out of the sample mold when the probe is being taken out of the molten metal.

The inlet region ahead of the mold inlet may be designed in the form of a funnel, it being possible for the dimensioning of the funnel to be chosen such that reliable removal of the steel-free slag sample is possible even in the case of very thin layers of slag. Under such conditions, a wide funnel diameter with a small funnel height is chosen, so that access is possible to a relatively large surface area of slag, which then finds its way via the inlet funnel into the sample chamber of relatively small diameter, so that the sample chamber is completely filled by slag in spite of the thin layer of slag. In this case, the volume of the inlet funnel is preferably greater than the volume of the sample mold.

Furthermore, the problem which the invention addresses is solved by the sample chamber being bounded by a metal plate, which may have a wall thickness of less than 2 mm. This small wall thickness of the metal plate avoids excessively quick cooling of the slag surface, as a result of lower thermal conduction, whereby cracking of the slag sample is prevented.

With the sample surface formed on the metal plate, direct analysis of the slag sample is possible without processing, or with only little processing. To facilitate sample analysis further, in the slag chamber a sample ring may be provided, which encloses and stabilizes the sample during transport and analysis and which is removed from the sample chamber together with the slag sample. This prevents the sample from being fractured by mechanical stresses, in particular when it is removed from the sample chamber. In addition, the sample ring permits exact fixing of the sample in the adapter of an automatic analyzer.

For sample removal, the probe according to the invention is dipped in through the slag, whereupon the sample mold is filled on account of the ferrostatic pressure. If this pressure is inadequate, the probe can be dipped in further. The filling of the sample mold may be assisted by generating a negative pressure. The smallest possible inside diameter of the mold inlet prevents the sample from running out once the sample chamber has been filled and the probe is being removed from the slag.

The sample ring may be formed of a multi-part construction, in order to facilitate separation of the sample ring and sample-if this is necessary. However, the sample preferably remains in the sample ring, as described above. In addition, the sample ring may have notches or grooves in order to increase the adherence of the sample in the ring and, as a result, prevent the sample from falling out.

In another embodiment of the invention, the mold and metal plate are arranged below the elevation of the slag inlet, which is preferably designed in the form of one or more lateral inlet openings. The slag running in from above then solidifies on the thin metal plate and thus forms a usable analysis surface. In this embodiment, too, a sample ring may be provided for the removal and protection of the slag sample, but this ring is, in this embodiment, arranged above the metal plate. This embodiment consequently also allows direct sample analysis without further processing or preparation of the slag sample for the adapter of the analyzer. In this embodiment, the analysis surface lying at the bottom proves to be a particular advantage, since gas bubbles located in the liquid slag rise upwards, so that the analysis surface has fewer gas bubbles and consequently provides an analysis surface of better quality.

This embodiment is likewise advantageous in slag sampling from a low bath depth, such as for example in the slag channel on a blast furnace.

The invention is explained in more detail below on the basis of an exemplary embodiment represented in the drawing.

DETAILED DESCRIPTION OF THE INVENTION

Figure 1:
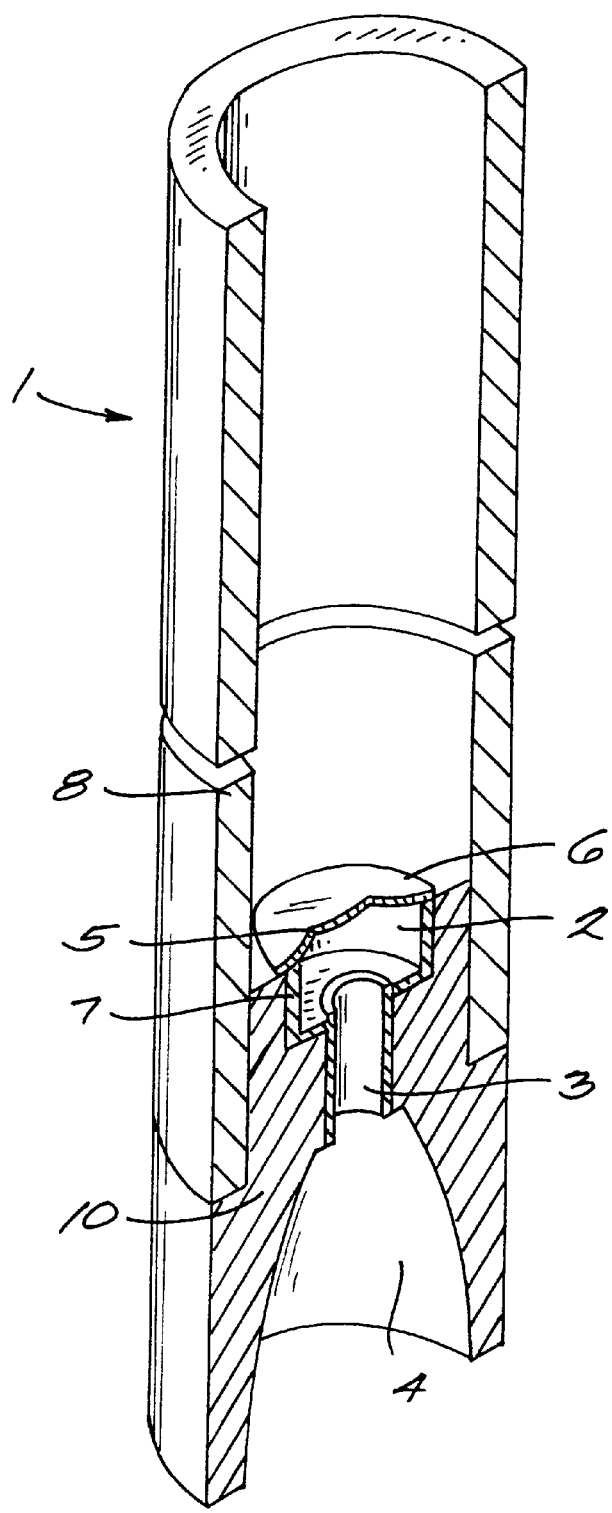
FIG. 1 shows a device according to the invention for the removal of slag samples, with a sample inlet arranged underneath a metal plate.

The device for slag sample removal comprises a cross-sectionally circular probe 1 with a sample chamber 2, a sold inlet 3 and an inlet funnel 4. The sample chamber 2 is bounded upwards, i.e. in the direction of the probe, by a metallic cooling plate 5. The sample removal unite 2, 3, 4, 5 is located in the lower region, i.e. facing the slag, of the probe 1, which in its upper region comprises a cardboard tube 8.

The sample chamber 2, arranged underneath the cooling plate 5, is connected to the inlet funnel 4 via the mold inlet 3. The mold inlet 3 has a small cross section in comparison with the cross section of the sample chamber and of the inlet funnel.

The sample chamber 2 is surrounded by a metal or ceramic sample ring 7, which encloses the slag sample even in the solidified state and can be removed with the latter from the probe.

For the removal of a sample, the probe is lowered into the metallurgical vessel 30, until it comes into contact with the surface of the slag in the region of the inlet funnel 4. The cross section and geometry of the inlet funnel 4 is chosen according to the thickness of the layer of slag 31, so that an adequate amount of slag can enter the sample chamber 2 without molten metal 32 penetrating into the sample chamber. In the case of a particularly thin layer of slag 31, therefore an inlet funnel with a particularly large cross section is chosen to be able to resort to the substance of as large a surface area of slag as possible.

As soon as the inlet funnel 4 has reached an adequate dipping depth into the steel molten metal 32, the slag rises into the sample chamber 2 via the mold inlet 3 on account of the ferrostatic pressure, the air located in the mold inlet and the sample chamber 2 escaping via venting openings 6. When the sample chamber 2 is filled with slag, the uppermost layer of slag comes into contact with the cooling plate 5, which is dimensioned with respect to its thickness such that the cooling process does not lead to cracking or rupturing of the solidified slag. The choice of the material of the cooling plate can also be varied for this purpose. The mold inlet 3, with its small Coors section, on the one hand prevents the slag sample from running out again and on the other hand produces a defined separating plane between molten metal and slag—even if the case of extremely thin layers of slag metal molten metal also gets into the slag inlet—so that the sample chamber is in any event kept free of metal molten metal.

The slag sample located in the sample chamber 2 after sample removal is bounded laterally by the sample ring 7, which reaches completely around the slag sample. The sample ring 7 is formed of a heat resistant material, usually metal and has on its inner surface, in contact with the sample, a surface structure which prevents the sample from falling out. This may be achieved, for example, by notches or grooves. After solidifying, the slag sample can be removed together with the sample ring 7 from the probe 1. The dimensions of the sample ring 7 are chosen such that it can be inserted directly into the adapter of an analyzer. On account of the use of the cooling plate 5, the sample has a surface which allows immediate analysis without prior processing of the slag sample. In addition, the fragile slag sample is protected, by the sample ring 7 when the sample is unpacked from the probe and also during transport.

The slag probe described above and represented in FIG. 1 consequently allows reliable slag sample removal, even if the probe is dipped in to a depth such that it enters the layer of molten metal, since only slag can enter the sample chamber on account of the geometrical relationships of the inlet funnel, the slag inlet and the sample chamber. In addition, the entry of the slag into the sample chamber, optionally, may be assisted by use of a suction pump.

Figure 2:
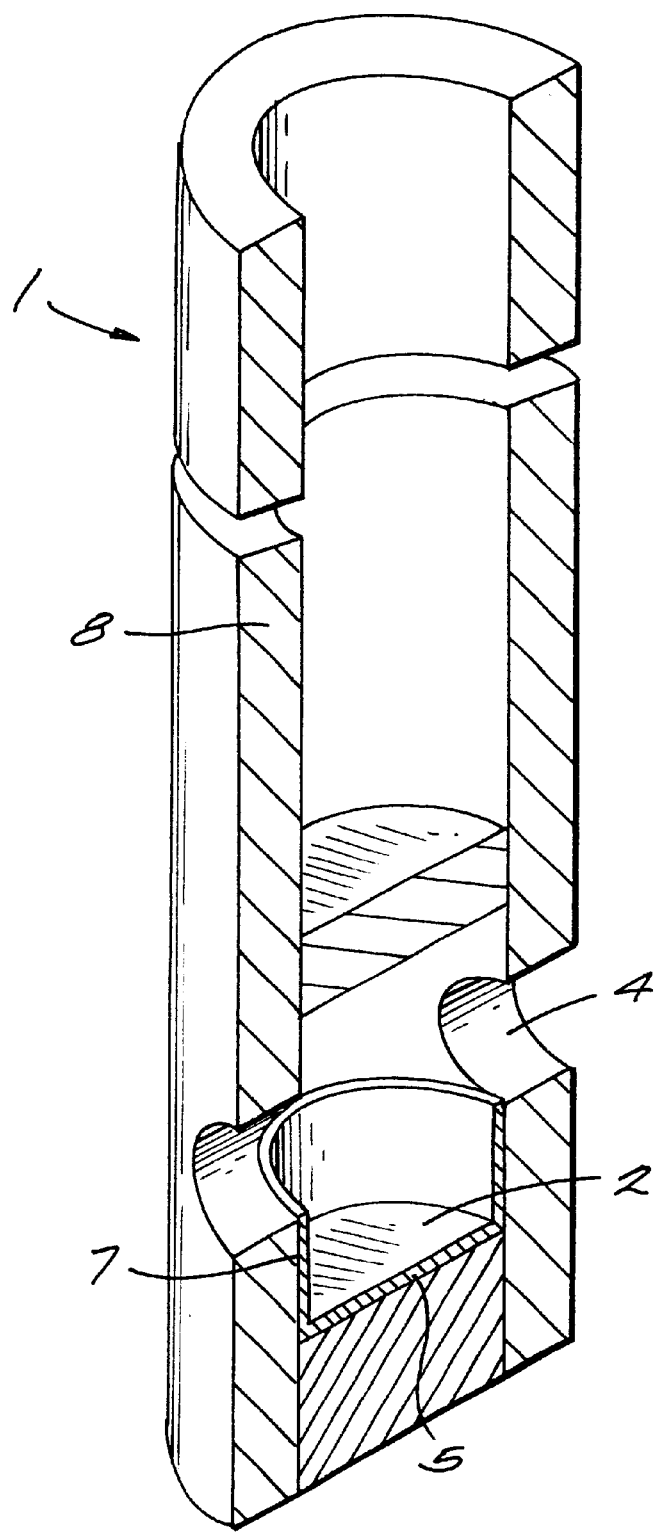
FIG. 2 shows a device according to the invention with slag inlets arranged above the metal plate.
Figure 3:
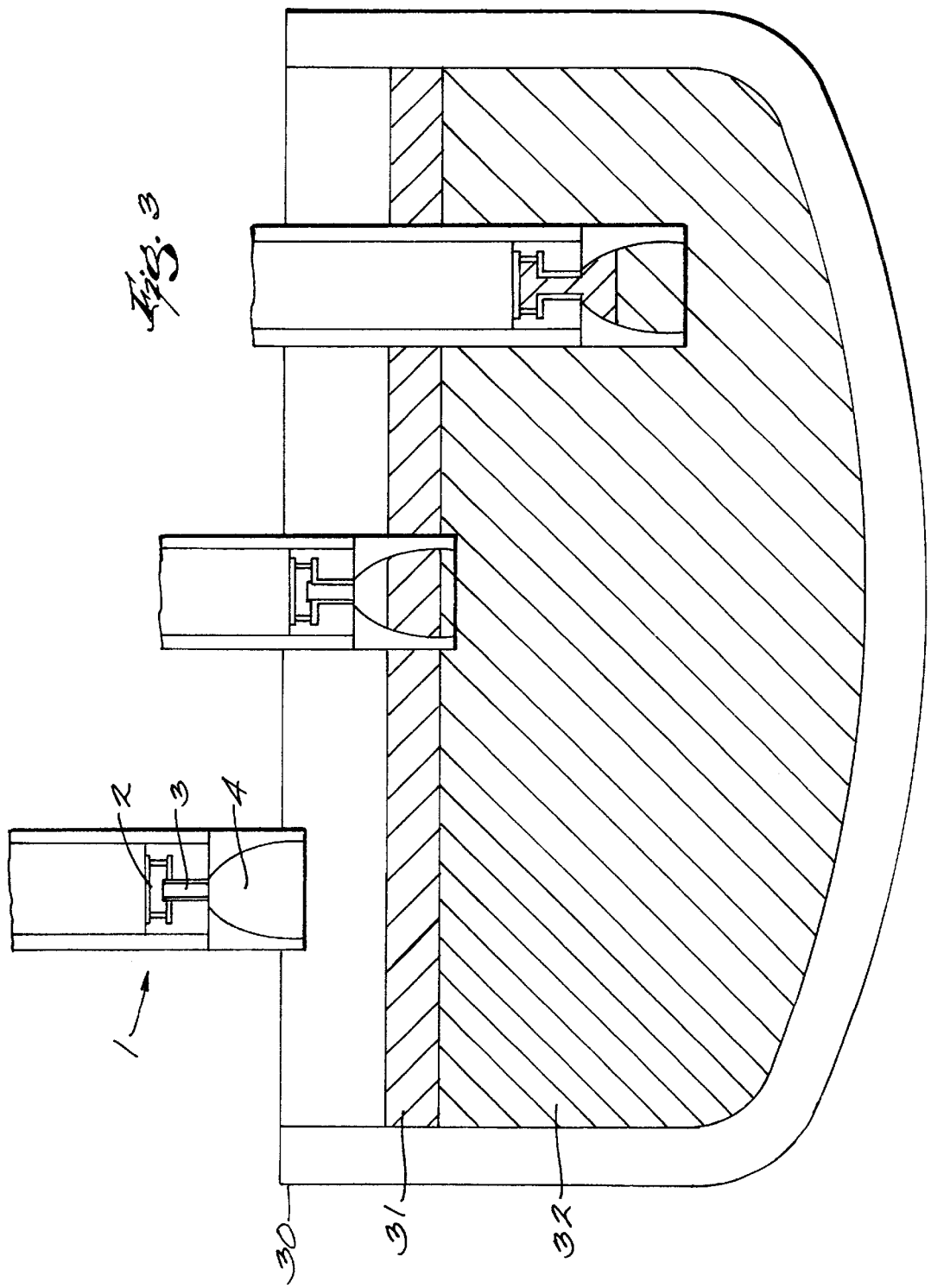
FIG. 3 shows a schematic representation of a sample being removed with a device according to the invention.

Another embodiment of the invention is represented in FIG. 2. In this embodiment, the mold inlet 3a, 3b is located above the sample chamber, so that when the probe is dipped into the layer of slag the slag flows into the sample chamber 2 and rests on the cooling plate 5, then arranged at the bottom of the sample chamber. In this embodiment, as well, the sample chamber 2 is bounded laterally by a sample ring 7, so that the slag sample can be removed from the probe and inserted into the adapter of an analyzer without any problem.

The sample itself has an analysis surface which is of high quality and free from unevenness caused by gas bubbles, since the gas bubbles in the liquid slag rise in the mold and consequently escape from the region of the cooling plate, which is subsequently used as the analysis surface.

When removing slag samples from a bath with a shallow bath depth, there is additionally the advantage that the mold is filled even if the ferrostatic pressure is very low on account of the low possible dipping depth.

The device according to the invention and the embodiments described can also be used in a combination probe, for example together with a blowing lance, a temperature measuring probe, a steel sample removal device, a bath level gauge, an e.m.f. measuring device and/or an oxygen cell. The device according to the invention may then be designed as a sublance and perform just one of many functions of the combination probe.

Figure 4:
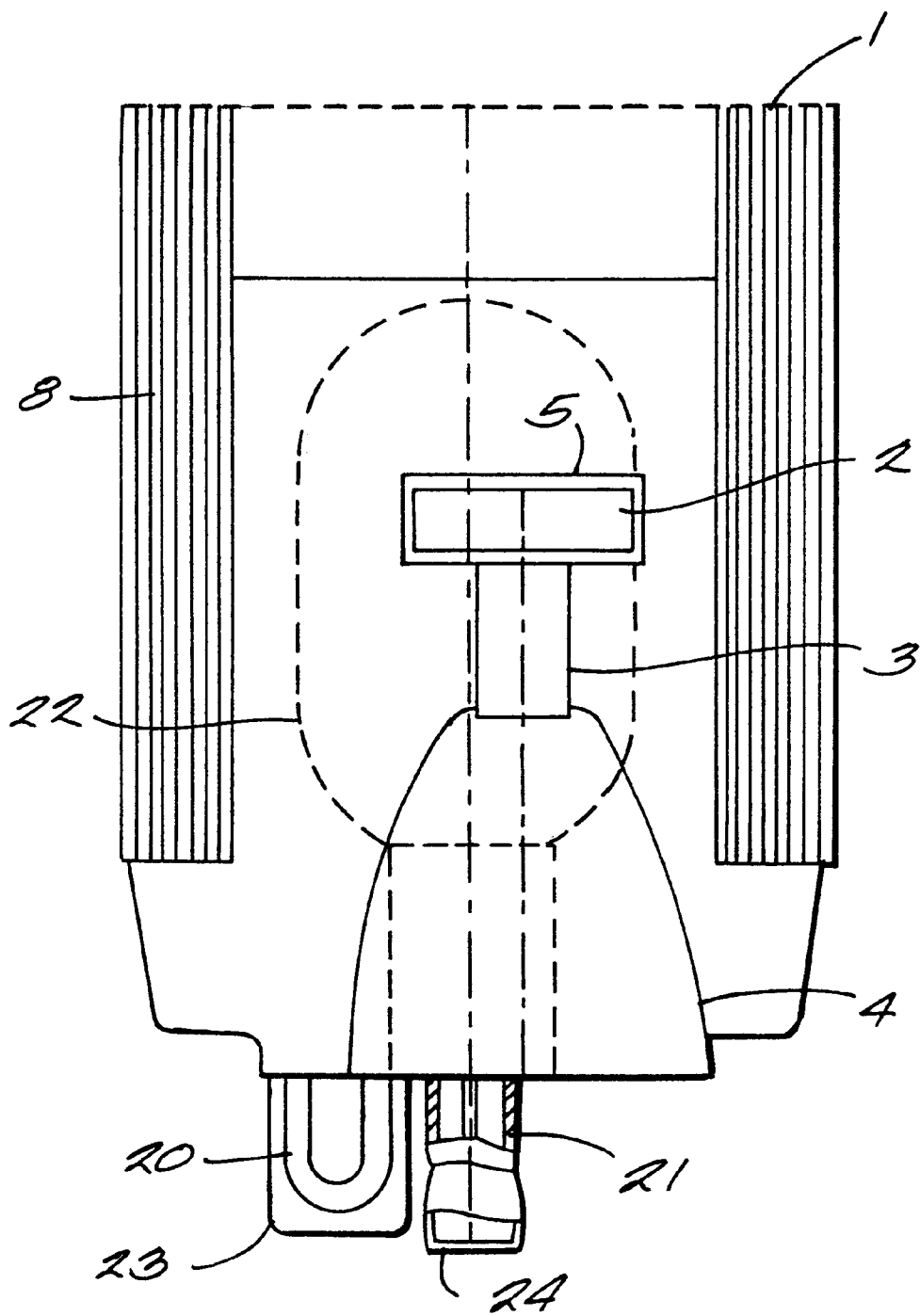
FIG. 4 shows a combination probe incorporating the device of FIG. 1.

Such a combination probe is represented in FIG. 4, with a thermocouple 20 and a steel sample inlet 21, with the associated mold 22. The thermocouple and steel sample inlet are protected by steel caps 23, 24 against the action of the slag during dipping.

In all the embodiments, the cooling or chill plate preferably consists of steel, but may alternatively consist of ceramic, non-ferrous metal or other materials, In the embodiment according to FIG. 2, the lateral inlets may also be located adjacent or at the same height as the sample mold.

Figure 5:
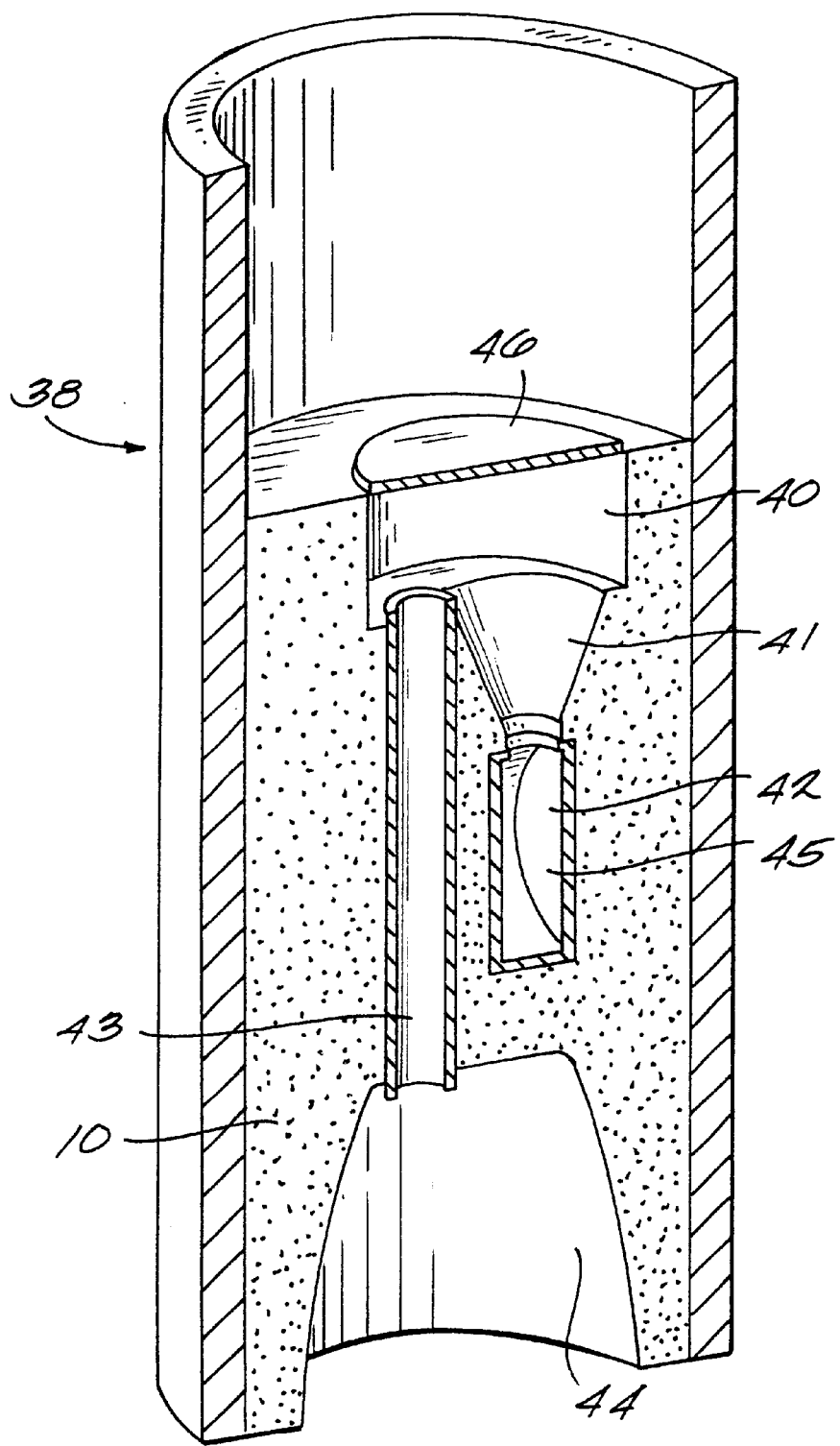
FIG. 5 is a central cross sectional view of a modified device showing a further embodiment of the invention.

Referring to FIG. 5 there is seen another form of probe 38 in accordance with another embodiment of the invention. As in the case of the earlier embodiments, the probe includes a heat resistant body 10 formed, for example, of a refractory or ceramic material or a baked sand-resin material. In this embodiment the slag flows upwardly, first, to an upper chamber 40 contained within the probe and thence downwardly through a funnel shaped passageway 41 into the mold chamber 42. The slag flows upwardly through an inlet passageway 43 which is lined with a heat resistant material. A quantity of slag is first captured in a funnel shaped bottom portion 44 of the probe which is of a substantially greater cross-sectional area than the inlet passageway 43. A cooling or chill plate 45 is preferably located on at least one side of the sample chamber 42. A heat resistant cover 46 is provided to close the top of the internal chamber 40.

It will be noted that the sampler 38 in many ways functions similarly to probe 1 which was described in detail above. In this embodiment, however, the fact that the slag flows downwardly into the sample chamber 42 thereby utilizes the force of gravity to ensure good contact between the molten slag and the side 45 of the sample chamber which is provided with a cooling plate, thereby assuring the formation of a smooth, uniform analysis surface on the slag sample.

The funnel shaped flow passage 41 connects the bottom of interior chamber 40 with the sample chamber 42. In the illustrated embodiment the flow passage 41 communicates with sample chamber 42 through an opening in the upper edge thereof.

What is claimed is:

1. A device for obtaining slag samples from molten metal comprising:
   a mold body defining a sample chamber;
   a mold inlet passage through a side of said mold body adjacent to the top of said sample chamber, said inlet passage being smaller in cross section than is the sample chamber;
   a cooling plate on a bottom wall of said sample chamber; and
   a sample ring removably located in the sample chamber and defining the side wall thereof.

2. A device according to claim 1 wherein the cooling plate comprises metallic or ceramic material.

3. A device according to claim 1 wherein the cooling plate has a thickness of less than 2 mm.

4. A device according to claim 1 wherein the cooling plate has a thickness of approximately 0.5 mm.

5. A device according to claim 3 wherein said sample ring is of a multipart design.

6. A device according to claim 1 wherein the diameter of the resultant slag sample is greater than the thickness thereof.

7. A device according to claim 1 in combination with a supporting cardboard tube and wherein additional molten metal measuring devices are also supported thereon.

8. A device for obtaining slag samples from molten metal comprising
   a mold body defining a sample chamber and
   a mold inlet through said mold body located below the sample chamber, and being smaller in cross section than said sample chamber;
   an inlet funnel disposed below and connected to said mold inlet, the inlet funnel having a volume greater than that of said sample chamber, said funnel having an opening with a cross section greater than that of said mold inlet, and
   a sample ring removably located in the sample chamber and defining the walls thereof.

9. A device according to claim 8 wherein said sample ring is of a multipart design.

10. A device for obtaining slag samples from molten metal comprising
    a mold body defining a sample chamber and
    a mold inlet through said mold body located below the sample chamber, and being smaller in cross section than said sample chamber; said mold inlet extending from a point below the sample chamber upwardly to an interior chamber located above said sample chamber and a flow channel connecting said interior chamber with said sample chamber whereby molten slag flows upwardly from said inlet funnel through said mold inlet into said interior chamber and subsequently downwardly into said sample chamber, and,
    an inlet funnel disposed below and connected to said mold inlet, the inlet funnel having a volume greater than that of said sample chamber, said funnel having an opening with a cross section greater than that of said mold inlet.

11. A device according to claim 10 wherein a cooling plate is provided on at least one wall of said sample chamber.

* * * * *